United States Patent
Bozkaya et al.

(10) Patent No.: US 11,224,395 B2
(45) Date of Patent: Jan. 18, 2022

(54) MEDICAL IMAGING SYSTEM AND METHOD FOR PROVIDING AN ENHANCED X-RAY IMAGE

(71) Applicant: KONINKLIJKE PHILIPS N.V., Eindhoven (NL)

(72) Inventors: Melike Bozkaya, Amsterdam (NL); Cherif Sahyoun, Eindhoven (NL); Fransciscus Joannes Leonardus Everaerts, Weert (NL); Bram Antonius Philomena Van Rens, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 547 days.

(21) Appl. No.: 14/429,203

(22) PCT Filed: Sep. 27, 2013

(86) PCT No.: PCT/IB2013/058926
§ 371 (c)(1),
(2) Date: Mar. 18, 2015

(87) PCT Pub. No.: WO2014/053973
PCT Pub. Date: Apr. 10, 2014

(65) Prior Publication Data
US 2015/0250438 A1    Sep. 10, 2015

Related U.S. Application Data

(60) Provisional application No. 61/710,061, filed on Oct. 5, 2012.

(51) Int. Cl.
*A61B 6/00*     (2006.01)
*A61B 6/12*     (2006.01)
(Continued)

(52) U.S. Cl.
CPC ............ *A61B 6/504* (2013.01); *A61B 5/0066* (2013.01); *A61B 5/0086* (2013.01); *A61B 5/026* (2013.01);
(Continued)

(58) Field of Classification Search
None
See application file for complete search history.

(56) References Cited

U.S. PATENT DOCUMENTS 7,087,893 B2    8/2006  Bechtel et al.
7,288,244 B2   10/2007  Van Langenhove et al.
(Continued)

FOREIGN PATENT DOCUMENTS

CN    100569187 A     3/2006
CN    101051387 A    10/2007
(Continued)

OTHER PUBLICATIONS

Rotger, D. et al. "Internal and external coronary vessel images registration", CCIA 2002, LNAI, pp. 408-418. Springer-Verlag Berlin Heidelberg 2002.
(Continued)

*Primary Examiner* — Luther Behringer
*Assistant Examiner* — Farouk A Bruce

(57) ABSTRACT

A medical imaging system with a screen, an X-ray imaging device having an X-ray interface and an intravascular data acquisition device having an intravascular interface provide enhanced X-ray images. For this purpose, the medical imaging system is adapted for overlaying an information set provided at the intravascular interface onto an X-ray image provided at the X-ray interface on user request for generating an enhanced X-ray image and for displaying the enhanced X-ray image on the screen.

18 Claims, 2 Drawing Sheets

(51) Int. Cl.
  *A61B 8/12* (2006.01)
  *A61B 5/00* (2006.01)
  *A61B 5/02* (2006.01)
  *A61B 5/026* (2006.01)
  *G06T 7/00* (2017.01)

(52) U.S. Cl.
  CPC ............ *A61B 5/02007* (2013.01); *A61B 6/12* (2013.01); *A61B 6/4417* (2013.01); *A61B 6/463* (2013.01); *A61B 6/5229* (2013.01); *A61B 6/5247* (2013.01); *A61B 8/12* (2013.01); *G06T 7/0012* (2013.01); *G06T 2207/10116* (2013.01); *G06T 2207/30101* (2013.01); *G06T 2210/41* (2013.01)

(56) References Cited

U.S. PATENT DOCUMENTS

| | | | |
|---|---|---|---|
| 7,855,723 | B2 | 12/2010 | Preiss et al. |
| 7,930,014 | B2 | 4/2011 | Huennekens et al. |
| 8,090,427 | B2 | 1/2012 | Eck et al. |
| 8,232,274 | B2 | 7/2012 | Ting et al. |
| 8,298,147 | B2 | 10/2012 | Huennekens et al. |
| 8,306,612 | B2 | 11/2012 | Macadam |
| 8,864,655 | B2 | 10/2014 | Ramamurthy et al. |
| 8,942,457 | B2 | 1/2015 | Florent et al. |
| 2004/0097805 | A1* | 5/2004 | Verard ............... A61B 1/00071 600/428 |
| 2006/0165270 | A1 | 7/2006 | Borgert et al. |
| 2006/0241465 | A1* | 10/2006 | Huennekens .......... A61B 6/504 600/458 |
| 2006/0262139 | A1 | 11/2006 | Rahn |
| 2007/0038081 | A1 | 2/2007 | Eck et al. |
| 2008/0058963 | A1 | 3/2008 | Garibaldi et al. |
| 2010/0094124 | A1 | 4/2010 | Schoonenberg et al. |
| 2011/0034801 | A1 | 2/2011 | Baumgart |
| 2011/0234630 | A1 | 9/2011 | Batman et al. |
| 2012/0004529 | A1 | 1/2012 | Tolkowsky et al. |
| 2012/0143045 | A1* | 6/2012 | Klingenbeck .......... A61B 5/062 600/424 |
| 2012/0230565 | A1 | 9/2012 | Steinberg et al. |
| 2012/0236032 | A1* | 9/2012 | Arvidsson ............. A61B 6/461 345/634 |
| 2013/0303888 | A1 | 11/2013 | Deladi et al. |

FOREIGN PATENT DOCUMENTS

| | | | |
|---|---|---|---|
| DE | 102007021061 | A1 | 11/2008 |
| EP | 1837828 | A2 | 9/2007 |
| JP | 2009160205 | A | 7/2009 |
| WO | 0174263 | A1 | 10/2001 |
| WO | 2004075756 | A1 | 9/2004 |
| WO | 2004093683 | A1 | 11/2004 |
| WO | 2005024729 | A1 | 3/2005 |
| WO | 2007002685 | A2 | 1/2007 |
| WO | 2008138009 | A1 | 11/2008 |
| WO | 2009023801 | A1 | 2/2009 |
| WO | 2010058398 | A2 | 5/2010 |
| WO | WO 2010058398 | A2 * | 5/2010 .......... G06T 7/0022 |
| WO | 2012042413 | A1 | 4/2012 |

OTHER PUBLICATIONS

Miura, Y., "New Applications for Cardiovascular Systems", Technical Report, Shimadzu Corporation (2002).

SYNC-RX Optimizing Coronary Imaging. http://www.sync-rx.com/EN/contents/page.aspx?contentPageID=14.

Bruining, N. et al, "Intravascular ultrasound registration/integration with coronary angiography." Cardiol Clin, vol. 27, No. 3, pp. 531-540, 2009.

* cited by examiner

MEDICAL IMAGING SYSTEM AND METHOD FOR PROVIDING AN ENHANCED X-RAY IMAGE

CROSS-REFERENCE TO PRIOR APPLICATIONS

This application is the U.S. National Phase application under 35 U.S.C. § 371 of International Application Serial No. PCT/IB2013/058926, filed on Sep. 27, 2013, which claims the benefit of U.S. Application Ser. No. 61/710,061, filed on Oct. 5, 2012. These applications are hereby incorporated by reference herein.

FIELD OF THE INVENTION

The present invention relates to a medical imaging system and a method for providing an enhanced X-ray image.

BACKGROUND OF THE INVENTION

For the evaluation and intervention of Coronary Artery Disease (CAD), the use of different medical modalities is known. X-ray, as one of the common modalities, is in use for the diagnosis of CAD and for guidance in interventional procedures. Thereby, X-ray images may provide a silhouette of the vessel lumen. For enhancing the information about a lesion, non-angiographic coronary lesion assessment tools or intravascular technologies, respectively, like intravascular ultrasound (IVUS), optical coherence tomography (OCT), fractional flow reserve (FFR), near-infrared spectroscopy (NIRS) and other tools may also be used in order to gather more information about the internal structure and function of the vessel and the plaque/tissue characteristics. Since from a technical imaging perspective, there is no direct relation between the information of the X-ray image data (i.e. global information) and intravascularly gathered data (i.e. local information), mental correlation of these two sets of data is necessary for a cardiologist.

SUMMARY OF THE INVENTION

Even though different modalities are commonly used for evaluation and intervention, however, the physician still needs to change his focus from one view to another, for example on two different screens, as well as to infer position of e.g. an IVUS probe when no X-ray image data is acquired.

Hence, there may be a need for improving the information collection in a multi-modality environment, such as with IVUS and angiography tools, for providing an optimal support of the physician.

This need may be met by a medical imaging system as defined in claim 1. Advantageous embodiments and improvements may be gathered from the subclaims and the following description.

An exemplary embodiment of a medical imaging system according to the invention may comprise a screen, an X-ray imaging device having an X-ray interface and an intravascular data acquisition device having an intravascular interface. The medical imaging system is adapted for overlaying an information set provided at the intravascular interface onto an X-ray image provided at the X-ray interface on user request for generating an enhanced X-ray image and for displaying the enhanced X-ray image on the screen.

As a first modality, the X-ray imaging device may be a common X-ray device, e.g. of a C-arm type, used for this kind of operation. By this measure, a catheter may be monitored during an interventional operation. Preferably, the X-ray imaging device may comprise a catheter tip tracking means adapted for identifying the location of the tip of a catheter on acquired X-ray images. Altogether, the X-ray imaging device shows the acquired X-ray images onto the X-ray screen.

The intravascular device may represent a second modality of operation tool and may show information and images on another screen, such as an intravascular screen.

A main idea of the present invention therefore lies in the combination of two different imaging modalities during an interventional procedure such that, for example, the physician may constantly be provided with the X-ray image data for enhancing the orientation and, on request, is provided with additional information derived from the second modality. The latter may consist of one of the previously mentioned modalities such as a non-angiographic coronary lesion assessment tool like IVUS, OCT, FFR, NIRS etc.

The medical imaging system according to the invention firstly overcomes the need of a mental match that the interventional cardiologists have to perform. It is not necessary to perform mental matching of X-ray data and intravascular data, because both data will be visualized in a combined/single view of the combined data. This, in turn, frees cognitive resources towards the clinical task. As intravascularly gathered data will be overlaid on the vessel tree, the visualization will provide an intuitive and quick access to the intravascular information. With the medical imaging system according to the invention, clearly more precise information is provided, e.g. regarding the vessel diameter size during stent deployment. Since X-ray is the only image that may be used during the deployment of stents, all the required information will be provided on top of, i.e. overlaid on, the X-ray image for supporting the physician in guiding the device placement.

The user request for generating the enhanced X-ray image may be input by any applicable means, such as by input means that are adapted for detecting an input command, by a certain setup, by a configuration file, by a certain operating state of the X-ray device, the intravascular device, peripheral components such as a screen grabbing mechanism (see below) etc.

In an exemplary embodiment the screen is an X-ray screen associated with the X-ray imaging device. The X-ray interface is at least one of an X-ray image data interface for providing image data and an X-ray screen interface for providing screen signals. Therefore, the medical imaging system according to the invention may provide the additional functionality of an enhanced X-ray image either if the X-ray imaging device is especially prepared for this purpose or if it merely constitutes a common X-ray imaging device having any interface connectable to a processing unit or a screen, which makes it retrofittable.

In an analogy, the intravascular interface may be an intravascular data interface for providing numerical intravascular data. Hence, the intravascular device may especially be prepared for constituting a main component of the medical imaging system according to the invention.

In an alternative embodiment, the medical imaging system may also be realized such that the intravascular interface is an intravascular screen interface for providing screen signals, and may further comprise an image acquisition device adapted for acquiring the image to be displayed of the intravascular imaging device. Even though the intravascular device was not especially prepared for this purpose, through the use of an image acquisition device a further processing of the intravascular information may be possible. In such an embodiment, it is not necessary for the intravascular imaging device to comprise a dedicated interface for delivering acquired image data to another device or system, e.g. a calculation unit. Instead, any intravascular imaging device may be used for constituting a core part of the medical imaging system according to the invention. The image acquisition device, that may be referred to as a screen grabber, may simply be a processing means for converting display signals primarily used for directly controlling the output of a screen attached to the intravascular imaging device, into digital image data of the required type that may fed into other devices. The image acquisition device may therefore comprise a suitable interface for connecting it to the X-ray imaging device and/or the calculation unit.

In an exemplary embodiment, the medical imaging system comprises a calculation unit, which is adapted for performing a co-registration of data acquired by the intravascular system and the X-ray data. The intravascular probe may comprise at least one marker that is detectable in the X-ray image. The visual orientation and size of the intravascular probe may be transformed to the actual X-ray image acquired by the X-ray imaging device. If necessary or required by the physician, the registered data of the intravascular device may simply be overlaid on the X-ray image, preferably in the vicinity of the at least one marker.

Further, the calculation unit may be adapted for tracking a catheter, e.g. a tip of a catheter, or an intravascular probe. This may be supported by using markers on the catheter or the intravascular probe with an increased detectability.

In another exemplary embodiment, the calculation unit is adapted for receiving image data from the intravascular device and overlaying it onto the acquired X-ray image data and transferring the enhanced X-ray image to the display unit.

Without any further specification, the information may be overlaid on any place on an available screen, such as an X-ray screen. For example, the information may be placed in a special, dedicated field of the X-ray screen, such as a dedicated screen column or bar, placed on a side or a top region of the respective screen. This may further be supported by the placement of a marker or another indication that shows where the information is applicable. In addition to that, a side panel, if existing, of the X-ray screen may also be used to show the information.

In an exemplary embodiment it may be an option to automatically determine or to initially select a suitable position for overlaying the image data from the intravascular device such that it neither obstruct the physician's main view nor distract from the main task that is to be accomplished. For this purpose a minimum distance from a detectable catheter tip or other intravascular device monitored by the X-ray imaging device, may be defined. The overlay of the intravascular image data is then performed under automatically maintaining at least this minimum distance, e.g. by the calculation unit. If the physician initially selects a suitable position for displaying/overlaying the information box, this position may further be automatically adjusted in case the actual distance is below the predetermined minimum distance.

In an exemplary embodiment, the calculation unit may be integrated into the intravascular imaging device or the X-ray imaging device. For this purpose, image data of the X-ray imaging device may be transferred to the intravascular device such that, for example, detected marker positions on the X-ray image may be used for the registration, or the images are processed directly in the X-ray imaging device.

In another exemplary embodiment, the intravascular device is adapted for determining local vascular dimensions and wherein the calculation unit is adapted for generating an information set and for overlaying this information set onto the X-ray image. For example, if a clinician requires information about a diameter of a certain branching in a vessel tree that cannot unambiguously be derived from the acquired X-ray image a support is provided by the intravascular imaging device. The determination of the local vascular dimensions may require a user interaction. The information may be overlaid in a selected, predetermined or automatically determined position, for example near a region of the catheter tip, such that the physician gets a very lean and clear indication without the need to be distracted by another screen and may thus enhance the performance. Instead of image data only the required information is shown to the physician and may thereby reduce a distraction level and clearly enhances the quality of information.

In a still further embodiment, the medical imaging system comprises at least one input means connected to the calculation unit, wherein the calculation unit is adapted for receiving an overlay command from the at least one input means and for overlaying data acquired by the intravascular imaging device onto the X-ray image depending on the user input on the at least one input means. The image data presented to the physician may be simply altered by requesting or interrupting the overlay of intravascular image data such that, exemplarily in certain situations, the physician is not distracted by information not necessary at the time. In a preferred embodiment, the at least one input means may be a toggle button, which may toggle between the display of the acquired X-ray image data without any overlay, the X-ray image data with the overlay of intravascular image data, the X-ray image data with overlay of dimensional measures of the intravascular image device and the X-ray image data with overlay of intravascular image data and dimensional measures of the intravascular image device at the same time. The physician is able to toggle between these different uses without having to look at the at least one input means as the respective toggle button may just be pressed consecutively until the desired view is presented. This further enhances the performance of the physician. It is clear that the toggle button is preferably a button that switches between view modes, which are maintained once they are selected. In alternative embodiments, a standard view may be predetermined and by pressing the toggle button only temporarily another view mode is activated, either a view mode that is maintained as long as the toggle button is pressed or which is maintained as long as a certain predetermined time period after pressing the button ends.

The invention further relates to a method for generating enhanced X-ray images, comprising the steps of acquiring X-ray images, generating intravascular information and overlaying an intravascular information set onto the X-ray images on user request. Thereby, the user request may include several different options. For instance, the user may request the overlay once, such that after the initial command for overlaying information it remains until a further command for stopping the overlay. In another alternative, the user may activate an overlay for a predetermined time interval such that after pressing a button the overlay takes place for a predetermined time only. Alternatively, the user may activate a switch having two or more discrete positions such that the request is maintained in one of the discrete positions.

Additionally, as explained above, the method may further comprise the step of co-registering the X-ray images and the intravascular information.

Still further, the method may further comprise the step of tracking a catheter or an intravascular probe. This may be supported by using at least one marker on a catheter or an intravascular probe. This may further be advantageous for determining a suitable/applicable position of the overlaid intravascular information for maintaining a minimum distance to the tracked catheter or intravascular probe.

It has to be noted that features and side effects of the present invention have been described with reference to different embodiments of the invention. However, a person skilled in the art will gather from the above and the following description that unless other notified in addition to any combination or features belonging to one embodiment also any combinations between features relating to different embodiments or to a manufacturing method is considered to be disclosed with this application.

DETAILED DESCRIPTION OF EMBODIMENTS

Figure 1:
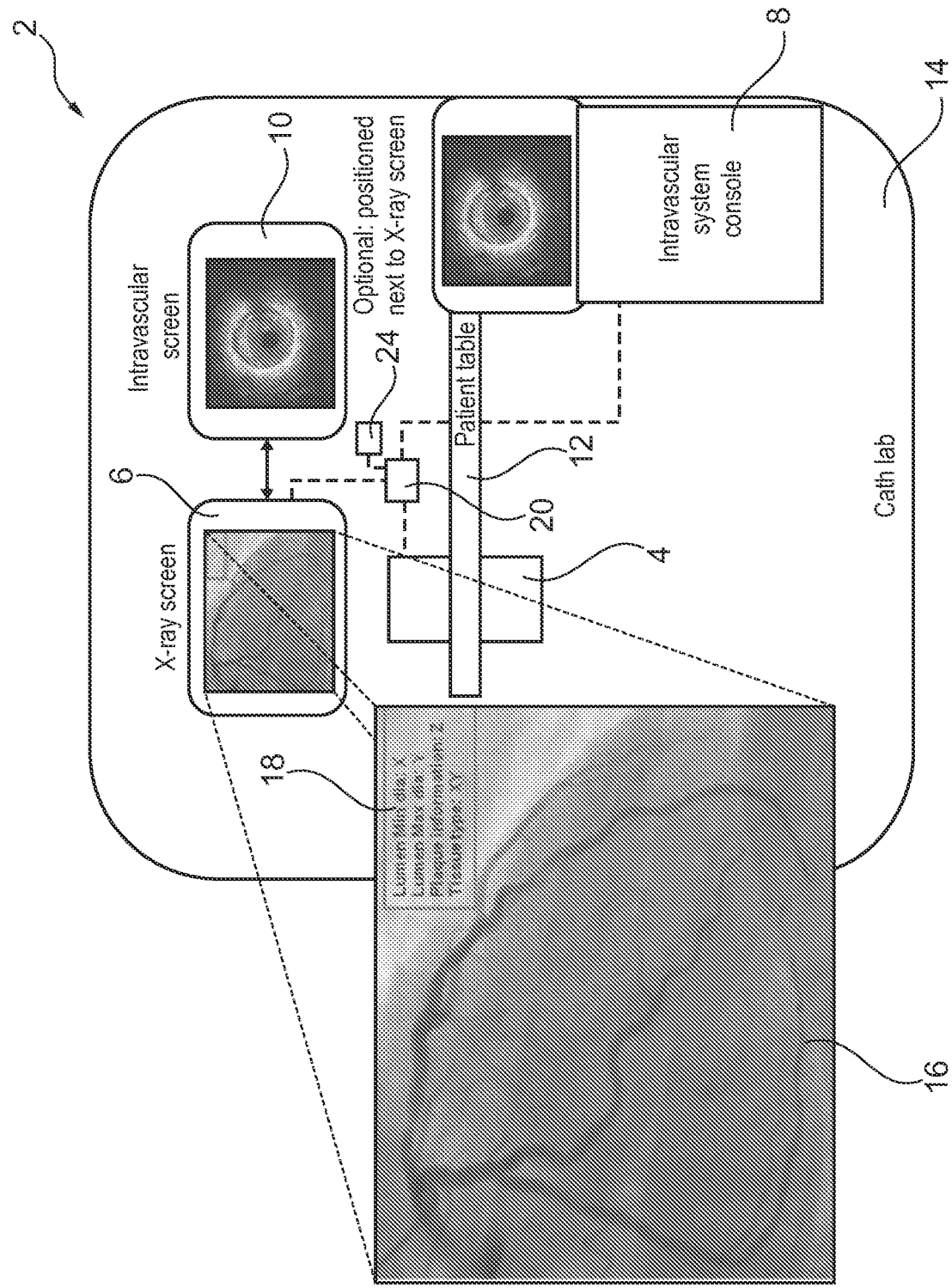
FIG. 1 shows a first exemplary embodiment of the medical imaging system with the capability of co-registration of two different modalities.

FIG. 1 exemplarily shows a general setup of a medical imaging system 2 comprising an X-ray imaging device 4 connected to an X-ray screen 6 as well as an intravascular device 8 connected to an intravascular screen 10. These components may be placed around a patient table 12 in a catheter lab 14.

According to the invention, the physician who conducts the interventional procedure primarily monitors the X-ray screen 6 as it is the only way to monitor a catheter tip in a vascular tree that preferably has been made visible by a contrast agent. The main image on the X-ray screen 6 is therefore a two- or three-dimensional image 16 of the region of interest.

On the other hand, by means of an intravascular device a more local area is monitored without X-rays but instead with other intravascular technologies such as IVUS, OCT, FFR and NIRS and other tools. These tools may provide images from a region at or around the catheter tip that may further support the clinician regarding more detailed information about plaque occurrences, the tissue type, diameters or other dimensional measures of the vascular tree where the catheter tip is placed.

In order to further improve the information flow to the physician, an information set is generated by the intravascular device 8 and is overlaid onto the X-ray image 16 as an information set box 18. This information set may comprise a data set, for example information about the lumen minimum diameter, the lumen maximum diameter, plaque information, tissue type, etc. Any other information that the intravascular device is capable of delivering may be overlaid, which may also include user annotations. For example, a physician indicates, annotates or marks a start region and an end region of the lesion by checking intravascular images. Of course, this information may also be overlaid on the X-ray images like start and end indications, wherein multiple overlays are also possible. For this purpose, the X-ray device 4, the X-ray screen 6, the intravascular device 8 may comprise a calculation unit 20, which may also be a separate component. For illustration purposes the calculation unit 20 is depicted as a separate box. It may comprise an interface into which the data can be delivered from the intravascular device 8 and/or the X-ray imaging device 4.

In this scenario it is assumed that a co-registration algorithm is applied after the acquisition of the X-ray and intravascular image/data generation. Depending on the co-registration algorithm the overlaid information set may consist of an image or not. The information set box 18 may further display an image shown on the intravascular screen 10 in case the physician requests it. The image is available due to the type of co-registration algorithm.

Since a co-registration algorithm is already applied, the views on the X-ray screen 6 and on the intravascular screen 10 are already synchronized during the review. The visualization of the catheter tip position may be enhanced automatically, e.g. by means of a marker, due to the use of the tip tracking algorithm. The marker position thereby indicates the location of the intravascularly acquired data, in this example a cross-sectional image, on the coronary tree.

The medical imaging system 2 thereby provides information from an X-ray modality and an intravascular modality. The overlaid data may further be updated as the location of the catheter tip, e.g. by a manual interaction, and hence, the intravascular data, changes. Moreover, this overlay information may also be visible during the stent deployment, e.g. on the tracked markers of the stent in the X-ray image, such that the confidence of the physician regarding the lesion location would be increased.

By means of a user input means 24, such as a toggle button, a switch or any other means through which a physician may input a command into the medical imaging system 2, the physician may switch between different modes of view. For example, the information set box 18 may include intravascular images, dimensional information, both types of information or it may be deactivated completely.

Figure 2:
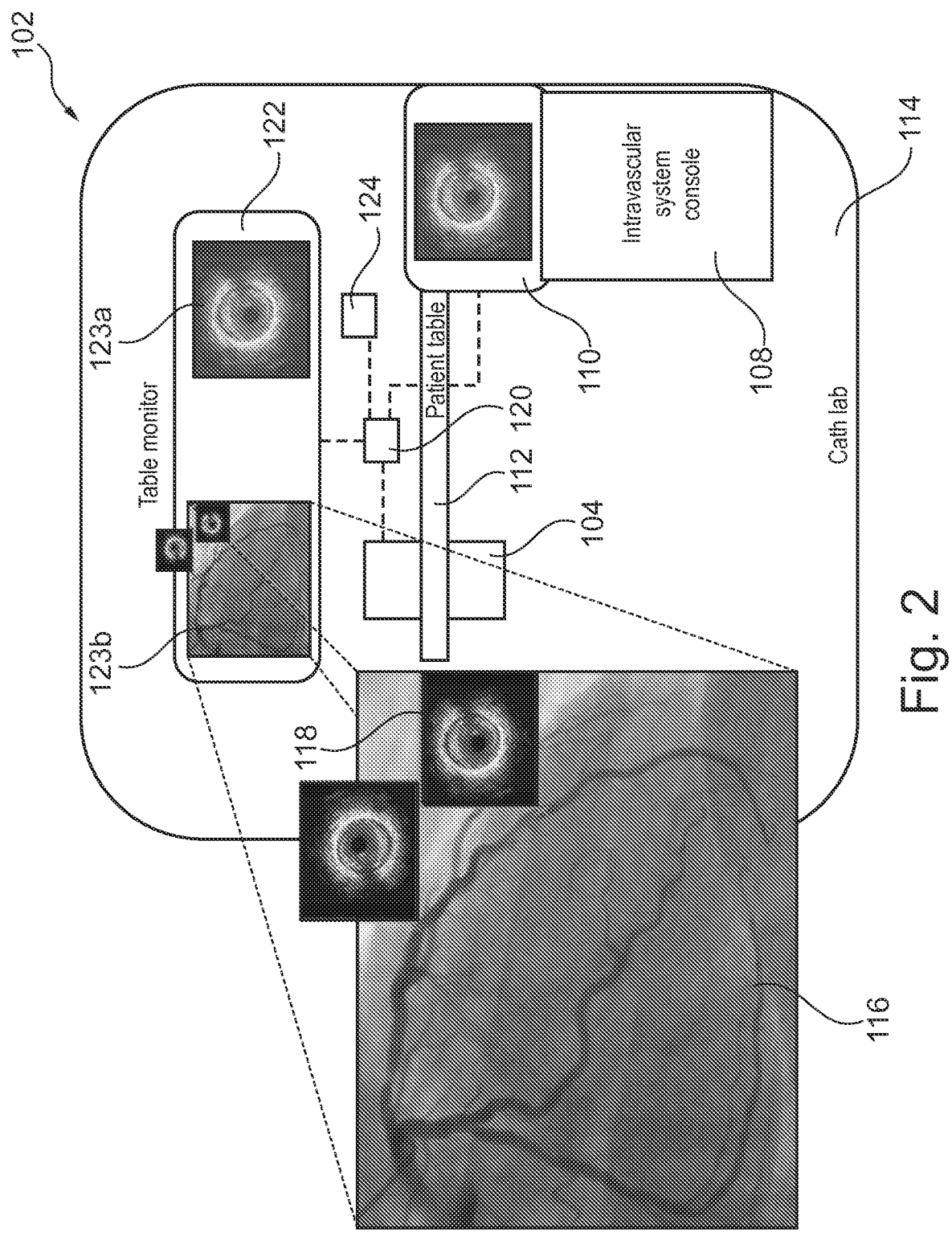
FIG. 2 shows a second exemplary embodiment of the medical imaging system without the capability of co-registration.

In FIG. 2 a medical imaging system 102 is shown that does not comprise the ability to conduct a co-registration. In this scenario it is an exemplary feature that a screen 110 of an intravascular device 108 is slaved to a table monitor 122 that may be connected to a dedicated calculation unit 120. An X-ray device 104 and an intravascular device 108 are independent from each other. In a preferred embodiment, the intravascular device 108 is able to give an explicit permission for slaving its screen 110 into the screen 122 in order to constitute a screen, view or image section 123a. Furthermore, the X-ray device 104 may have the capability to provide its view data as a screen, view or image section 123b to the table monitor 122 and displays an X-ray view 116. It is clear, that the table monitor 122 may also be a part of the X-ray device 104 or of the intravascular device 108.

During the acquisition, i.e. the X-ray image acquisition and the intravascular image/data generation, the physician checks either the view section 123a on the table monitor 122 transferred from the intravascular device 108 or the screen 110 of the intravascular device if it is positioned in a vicinity of the X-ray device 104. Whenever the physician recognizes an image that motivates to take a closer look, a user input means 124 may be pressed. This input triggers the overlay of the intravascular view presented on the intravascular screen 110 or in the view section 123a of the table monitor 122.

Exemplarily, the intravascular device 108 is connected to a screen grabbing mechanism that may be realized within the calculation unit 120, such that the intravascular image generated by the intravascular device 108 is shown not only on the intravascular screen 110, but also on the table monitor 122 as a view section 123*a* through the transfer by means of a network or any other data communication line that is capable of transferring images in real time. This view section 123*a* may then be overlaid onto the X-ray view section 123*b*.

Also, the intravascular device 108 may comprise an interface, which is not shown in FIG. 2, that allows to transfer the intravascular view to a dedicated table monitor 122 such that the view section 123*a* is constituted. The calculation unit 120 may then be adapted for grabbing the view section 123*a* from the table monitor 122 and generate an information set box 118 for overlaying onto the X-ray image view section 123*b*.

Such a grabbed image may, as with the exemplary embodiment presented in FIG. 1, correlated with the position of the catheter tip that is tracked on the X-ray image 116. Therefore, this grabbed intravascular image is correlated with an X-ray frame and this correlation is done based on a tracked tip of the catheter. After the acquisition finishes, the review phase starts and the grabbed and correlated intravascular images are overlaid on the X-ray image 116 in relation with the position of the catheter tip.

Both embodiments of FIGS. 1 and 2 include user interaction mechanisms like clicking and dragging the marker and/or thumb nail images over the vessel. The movement of the marker on the vessel updates the information shown on the vessel and reflects the local information gathered on the location of the marker.

Finally, it is to be noted that herein the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 2 medical imaging system
4 X-ray imaging device
6 X-ray screen
8 intravascular device
10 intravascular screen
12 patient table
14 catheter lab
16 two-dimensional X-ray images or three-dimensional images
18 information set box
20 calculation unit
24 user input means
102 medical imaging system
104 X-ray imaging device
108 intravascular device
110 intravascular screen
112 patient table
114 catheter lab
116 two-dimensional X-ray images or three-dimensional images
118 information set box
120 calculation unit
122 table monitor
123*a* view section
123*b* view section
124 user input means

The invention claimed is:

1. A medical imaging system, comprising:
a processor that processes instructions;
at least one screen;
an X-ray imaging device that provides an X-ray image; and
an intravascular device that provides an information set,
wherein, when executed by the processor, the instructions cause the medical imaging system to perform a process comprising:
tracking a tracked device on the X-ray image;
overlaying the information set provided by the intravascular device onto the X-ray image provided by the X-ray imaging device for generating an enhanced X-ray image that includes a representation of the tracked device and the information set and for displaying the enhanced X-ray image on the at least one screen, and
maintaining a pre-defined positive minimum distance between the representation of the tracked device and the information set in the enhanced X-ray image while the tracked device is being moved and tracked by automatically adjusting a position of the information set in the enhanced X-ray image to maintain the pre-defined positive minimum distance.

2. The medical imaging system of claim 1,
wherein the at least one screen comprises an X-ray screen associated with the X-ray imaging device, and
wherein the X-ray imaging device comprises an interface for displaying image data.

3. The medical imaging system of claim 1,
wherein the intravascular device comprises an interface for providing numerical intravascular data.

4. The medical imaging system of claim 1,
wherein the intravascular device is configured to provide screen signals, and to acquire an image to be displayed based on the screen signals.

5. The medical imaging system of claim 1,
wherein the medical imaging system is adapted for co-registering data acquired by the intravascular device and the X-ray imaging device, and
the overlaying by the medical imaging system is based on the co-registering of the data acquired by the intravascular device and the X-ray imaging device.

6. The medical imaging system of claim 1,
wherein the tracked device comprises a catheter or an intravascular probe.

7. The medical imaging system of claim 1,
wherein the X-ray imaging device is integrated into the medical imaging system.

8. The medical imaging system of claim 1,
wherein the intravascular device is adapted for determining local vascular dimensions and providing the local vascular dimensions in the information set.

9. The medical imaging system of claim 1, further comprising:
an input,
wherein the medical imaging system is adapted for receiving the user request by at least one of the input and a configuration file.

10. The medical imaging system of claim 9,
wherein the input comprises a toggle switch for consecutively toggling the enhanced X-ray image to overlay numerical intravascular information or intravascular image data, or for removing the information set.

11. The medical imaging system of claim 1,
wherein the at least one screen comprises an X-ray screen associated with the X-ray imaging device, and
wherein the X-ray imaging device comprises an X-ray screen interface for displaying screen signals.

12. A method for generating enhanced X-ray images, comprising:
acquiring at least one X-ray image;
generating intravascular information;
determining respective positions of the X-ray images and overlaying, on a screen and automatically or upon user request, an intravascular information set on the screen based on the intravascular information onto the at least one X-ray image at the respective positions;
tracking a device in the at least one X-ray image as a tracked device; and
maintaining at least a predefined positive minimum distance from the intravascular information set at the respective positions to a representation of the tracked device in the at least one X-ray image while the tracked device is being moved and tracked by automatically adjusting a position of the intravascular information set in the enhanced X-ray image to maintain the predefined positive minimum distance.

13. The method of claim 12, further comprising:
co-registering the X-ray images and the intravascular information,
wherein the overlaying is based on the co-registering of the X-ray images and the intravascular information.

14. The method of claim 12,
wherein the screen comprises an X-ray screen associated with an X-ray imaging device that acquires the at least one X-ray image.

15. The method of claim 12,
wherein the intravascular information set is provided from an intravascular device and includes numerical intravascular data.

16. The method of claim 12, further comprising:
co-registering data acquired by an intravascular device and an X-ray imaging device,
wherein the overlaying of the intravascular information set is based on the co-registering of the data acquired by the intravascular device and the X-ray imaging device.

17. The method of claim 12,
wherein the tracked device comprises a catheter or an intravascular probe.

18. The method of claim 12, further comprising:
determining, by an intravascular device, local vascular dimensions, and
providing the local vascular dimensions in the intravascular information set.

* * * * *